(12) United States Patent
Hopper et al.

(10) Patent No.: US 8,116,869 B2
(45) Date of Patent: *Feb. 14, 2012

(54) CARDIOPULMONARY FUNCTIONAL STATUS ASSESSMENT VIA METABOLIC RESPONSE DETECTION BY IMPLANTABLE CARDIAC DEVICE

(75) Inventors: Donald L. Hopper, Maple Grove, MN (US); Bruce Wilkoff, Chagrin Falls, OH (US); Richard Morris, Hinckley, OH (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 877 days.

This patent is subject to a terminal disclaimer.

(21) Appl. No.: 12/139,933

(22) Filed: Jun. 16, 2008

(65) Prior Publication Data

US 2008/0249586 A1 Oct. 9, 2008

Related U.S. Application Data

(63) Continuation of application No. 10/917,235, filed on Aug. 12, 2004, now Pat. No. 7,389,143.

(51) Int. Cl.
*A61N 1/00* (2006.01)
(52) U.S. Cl. ...................................................... 607/19
(58) Field of Classification Search .................. 607/18, 607/19
See application file for complete search history.

(56) References Cited

U.S. PATENT DOCUMENTS

| | | | |
|---|---|---|---|
| 4,622,980 A | 11/1986 | Kunig | |
| 5,249,572 A * | 10/1993 | Bonnet | 607/20 |
| 5,511,553 A | 4/1996 | Segalowitz | |
| 5,645,575 A | 7/1997 | Stangl et al. | |
| 5,755,741 A | 5/1998 | Vogel | |
| 5,800,469 A | 9/1998 | Nappholz | |
| 5,836,987 A | 11/1998 | Baumann et al. | |
| 5,836,988 A | 11/1998 | Cooper et al. | |
| 5,891,176 A | 4/1999 | Bornzin | |
| 5,931,858 A | 8/1999 | Kadhiresan et al. | |
| 6,016,443 A | 1/2000 | Ekwall et al. | |
| 6,045,513 A | 4/2000 | Stone et al. | |
| 6,161,042 A | 12/2000 | Hartley et al. | |
| 6,190,324 B1 | 2/2001 | Kieval et al. | |
| 6,221,011 B1 | 4/2001 | Bardy | |
| 6,233,486 B1 | 5/2001 | Ekwall et al. | |
| 6,259,948 B1 | 7/2001 | Florio et al. | |

(Continued)

FOREIGN PATENT DOCUMENTS

WO WO-98/34537 A1 8/1998

(Continued)

OTHER PUBLICATIONS

"U.S. Appl. No. 11/852,845, Notice of Allowance mailed Sep. 20, 2010", 4 pgs.

(Continued)

*Primary Examiner* — Eric D. Bertram
(74) *Attorney, Agent, or Firm* — Schwegman, Lundberg & Woessner, P.A.

(57) ABSTRACT

An implantable cardiac device is configured and programmed to assess a patient's cardiopulmonary function by evaluating the patient's minute ventilation response. Such evaluation may be performed by computing a minute ventilation response slope, defined as the ratio of an incremental change in minute ventilation to an incremental change in measured activity level. The minute ventilation response slope may then be compared with a normal range to assess the patient's functional status.

20 Claims, 2 Drawing Sheets

U.S. PATENT DOCUMENTS

| | | | |
|---|---|---|---|
| 6,264,606 B1 | 7/2001 | Ekwall et al. | |
| 6,273,856 B1 | 8/2001 | Sun et al. | |
| 6,351,672 B1 | 2/2002 | Park et al. | |
| 6,371,922 B1 | 4/2002 | Baumann et al. | |
| 6,381,493 B1 | 4/2002 | Stadler et al. | |
| 6,408,208 B1 | 6/2002 | Sun | |
| 6,411,850 B1 | 6/2002 | Kay et al. | |
| 6,438,408 B1 | 8/2002 | Mulligan et al. | |
| 6,438,409 B1 | 8/2002 | Malik et al. | |
| 6,459,929 B1* | 10/2002 | Hopper et al. | 600/513 |
| 6,459,934 B1 | 10/2002 | Kadhiresan | |
| 6,490,485 B1 | 12/2002 | Sun et al. | |
| 6,519,495 B1* | 2/2003 | Sun et al. | 607/18 |
| 6,529,771 B1 | 3/2003 | Kieval et al. | |
| 6,539,249 B1 | 3/2003 | Kadhiresan et al. | |
| 6,572,557 B2* | 6/2003 | Tchou et al. | 600/483 |
| 6,645,153 B2 | 11/2003 | Kroll et al. | |
| 6,668,188 B2 | 12/2003 | Sun et al. | |
| 6,708,061 B2 | 3/2004 | Salo et al. | |
| 6,738,667 B2 | 5/2004 | Deno et al. | |
| 6,741,885 B1 | 5/2004 | Park et al. | |
| 6,752,765 B1 | 6/2004 | Jensen et al. | |
| 6,754,528 B2 | 6/2004 | Bardy et al. | |
| 6,823,214 B1 | 11/2004 | Sun et al. | |
| 6,839,593 B1 | 1/2005 | Sun et al. | |
| 6,904,313 B1 | 6/2005 | Snell | |
| 6,922,585 B2 | 7/2005 | Zhou et al. | |
| 6,961,615 B2 | 11/2005 | Kroll et al. | |
| 6,970,743 B2 | 11/2005 | Weinberg et al. | |
| 6,990,375 B2 | 1/2006 | Kloss et al. | |
| 7,016,730 B2 | 3/2006 | Ternes | |
| 7,031,766 B1 | 4/2006 | Paris | |
| 7,031,772 B2 | 4/2006 | Condie et al. | |
| 7,043,294 B1 | 5/2006 | Paris | |
| 7,070,568 B1 | 7/2006 | Koh | |
| 7,092,758 B2 | 8/2006 | Sun et al. | |
| 7,094,207 B1 | 8/2006 | Koh | |
| 7,155,281 B1 | 12/2006 | Fayram | |
| 7,167,743 B2 | 1/2007 | Heruth et al. | |
| 7,171,271 B2 | 1/2007 | Koh et al. | |
| 7,177,684 B1 | 2/2007 | Kroll et al. | |
| 7,194,305 B1 | 3/2007 | Salo et al. | |
| 7,207,947 B2 | 4/2007 | Koh et al. | |
| 7,269,458 B2 | 9/2007 | Kadhiresan et al. | |
| 7,277,756 B2 | 10/2007 | Smith et al. | |
| 7,389,143 B2 | 6/2008 | Hopper et al. | |
| 7,869,877 B2 | 1/2011 | Veerichetty et al. | |
| 2002/0151936 A1* | 10/2002 | Kloss et al. | 607/14 |
| 2003/0060854 A1* | 3/2003 | Zhu | 607/25 |
| 2003/0149453 A1 | 8/2003 | Kroll et al. | |
| 2003/0204147 A1 | 10/2003 | Condie et al. | |
| 2004/0073093 A1 | 4/2004 | Hatlestad | |
| 2004/0127944 A1 | 7/2004 | Casset | |
| 2004/0133079 A1 | 7/2004 | Mazar et al. | |
| 2004/0181260 A1 | 9/2004 | Anderson et al. | |
| 2005/0065443 A1 | 3/2005 | Ternes | |
| 2005/0090719 A1 | 4/2005 | Scheiner et al. | |
| 2006/0030892 A1 | 2/2006 | Kadhiresan et al. | |
| 2006/0036290 A1 | 2/2006 | Hopper et al. | |
| 2006/0200204 A1 | 9/2006 | Daum et al. | |
| 2006/0265019 A1 | 11/2006 | Sun et al. | |
| 2006/0293604 A1 | 12/2006 | Carlson et al. | |
| 2007/0021678 A1 | 1/2007 | Beck et al. | |
| 2008/0004668 A1 | 1/2008 | Kadhiresan et al. | |

FOREIGN PATENT DOCUMENTS

| | | |
|---|---|---|
| WO | WO-01/23040 A1 | 4/2001 |
| WO | WO-2005/037077 A2 | 4/2005 |
| WO | WO-2007/011565 A1 | 1/2007 |

OTHER PUBLICATIONS

"U.S. Appl. No. 10/914,632, Supplemental Notice of Allowance mailed Jun. 11, 2007", 4 pgs.

"U.S. Appl. No. 10/914,632, Final Office Action mailed Nov. 8, 2006", 9 pgs.

"U.S. Appl. No. 10/914,632, Non-Final Office Action mailed Jun. 7, 2006", 9 pgs.

"U.S. Appl. No. 10/914,632, Notice of Allowance mailed May 9, 2007", 6 pgs.

"U.S. Appl. No. 10/914,632, Response filed Feb. 8, 2007 to Final Office Action mailed Nov. 8, 2006", 8 pgs.

"U.S. Appl. No. 10/914,632, Response filed Oct. 10, 2006 to Non Final Office Action mailed Jun. 7, 2006", 7 pgs.

"U.S. Appl. No. 10/917,235, Final Office Action mailed Dec. 22, 2006", 9 pgs.

"U.S. Appl. No. 10/917,235, Non-Final Office Action mailed Jun. 7, 2006", 6 pgs.

"U.S. Appl. No. 10/917,235, Non-Final Office Action mailed Jun. 7, 2007", 10 pgs.

"U.S. Appl. No. 10/917,235, Response filed May 21, 2007 to Final Office Action mailed Dec. 22, 2006", 8 pgs.

"U.S. Appl. No. 10/917,235, Response filed Nov. 7, 2007 to Non-Final Office Action mailed Jun. 7, 2007", 9 pgs.

"U.S. Appl. No. 10/917,235 Response filed Oct. 10, 2006 to Non-Final Office Action mailed Jun. 7, 2006", 10 pgs.

"U.S. Appl. No. 10/917,235, Notice of Allowance mailed Feb. 12, 2008", 7 pgs.

"U.S. Appl. No. 11/184,327, Response filed Mar. 13, 2008 to Restriction Requirement mailed Feb. 12, 2008", 14 pgs.

"U.S. Appl. No. 11/184,327, Response filed Sep. 29, 2008 to Non-Final Office Action mailed Apr. 1, 2008", 14 pgs.

"U.S. Appl. No. 11/184,327, Restriction Requirement mailed Feb. 12, 2008", 6 pgs.

"U.S. Appl. No. 11/184,327, Non-Final Office Action mailed Apr. 1, 2008", 13 pgs.

"International Search Report and Written Opinion for Application No. PCT/US2006/026660, mailed Nov. 10, 2006", 12 pgs.

Buller, N. P., et al., "Mechanism of the increased ventilatory response to exercise in patients with chronic heart failure", *British Heart Journal*, 63(5), (May 1990), 281-283.

Francis, D. P., et al., "Cardiopulmonary exercise testing for prognosis in chronic heart failure continuous and independent prognostic value from VE/VCO$_2$ slope and peak VO(2)", *Eur Heart J.*, 21(2), (Jan. 2000), 154-161.

Kadhiresan, V., et al., "Cardiopulmonary Functional Status Assessment Via Heart Rate Response Detection by Implantable Cardiac Device", U.S. Appl. No. 11/852 845, filed Sep. 10 2007, 25 pgs.

Keteyian, S. J., et al., "Effects of exercise training on chronotropic incompetence in patients with heart failure", *American Heart Journal*, 138(2 Pt 1), (Aug. 1999), 233-240.

Myers, J., et al., "Influence of high-intensity exercise training on the ventilatory response to exercise in patients with reduced ventricular function", *Medicine & Science in Sports & Exercise*, 31(7), (Jul. 1999), 929-937.

Sullivan, M. J., "Relation Between Central and Peripheral Hemodynamics During Exercise in Patients with Chronic Heart Failure Muscle Blood Flow is Reduced With Maintenance of Arterial Perfusion Pressure", *Circulation*, 80(4), (Oct. 1989), 769-781.

Weber, K. T., et al., "Oxygen Utilization and Ventilation During Exercise in Patients with Chronic Cardiac Failure", *Circulation*, 65(6), (Jun. 1982), 1213-1223.

"U.S. Appl. No. 11/852,745, Preliminary Amendment filed Jun. 23, 2010", 7 pgs.

"U.S. Appl. No. 11/852,845, Non Final Office Action mailed Aug. 13, 2009", 8 pgs.

"U.S. Appl. No. 11/852,845, Notice of Allowance mailed Mar. 25, 2010", 4 pgs.

"U.S. Appl. No. 11/852,845, Response filed Nov. 13, 2009 to Non Final Office Action mailed Aug. 13, 2009", 11 pgs.

* cited by examiner

CARDIOPULMONARY FUNCTIONAL STATUS ASSESSMENT VIA METABOLIC RESPONSE DETECTION BY IMPLANTABLE CARDIAC DEVICE

CROSS REFERENCE TO RELATED APPLICATION

This application is a continuation of U.S. application Ser. No. 10/917,235, filed Aug. 12, 2004, now issued as U.S. Pat. No. 7,389,143, the specification of which is herein incorporated by reference.

FIELD OF THE INVENTION

The present disclosure pertains to cardiac rhythm management devices such as pacemakers and implantable cardioverter/defibrillators.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers have been used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction.

In pacemaker patients who are chronotropically incompetent (e.g., sinus node dysfunction), the heart rate is determined solely by the pacemaker in the absence of intrinsic cardiac activity. That heart rate is determined by the programmed escape intervals of the pacemaker which cause paces to be delivered to the atria and/or ventricles, depending upon the pacing mode, if no intrinsic beats occur before expiration of the escape intervals. Pacing the heart at a fixed rate as determined by the length of the programmed escape intervals, however, does not allow the heart rate to increase with increased metabolic demand. It is for this reason that rate-adaptive pacemakers have been developed which vary the programmed escape intervals in accordance with one or more physiological parameters related to metabolic demand such as obtained from an accelerometer or minute ventilation sensor. In chronotropically competent patients in need of ventricular pacing, on the other hand, atrial triggered pacing modes such as DDD/R or VDD/R are desirable because they allow the pacing to track the physiologically normal atrial rhythm, which causes cardiac output to be responsive to the metabolic needs of the body. For this latter group of patients, the pacemaker is normally programmed so that the atrial rate is overridden by an atrial or ventricular pace only if the atrial rate drops to a level considered unsafe.

Pacing therapy can also be used in the treatment of heart failure, which refers to a clinical syndrome in which an abnormality of cardiac function causes a below normal cardiac output that can fall below a level adequate to meet the metabolic demand of peripheral tissues. When uncompensated, it usually presents as congestive heart failure due to the accompanying venous and pulmonary congestion. Heart failure can be due to a variety of etiologies with ischemic heart disease being the most common. It has been shown that some heart failure patients suffer from intraventricular and/or interventricular conduction defects (e.g., bundle branch blocks) such that their cardiac outputs can be increased by improving the synchronization of ventricular contractions with electrical stimulation. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

The status of a patient's cardiopulmonary function may be defined as the extent to which the patient's heart and lungs are able to adequately supply the body's tissue with oxygen to meet metabolic demand. Patients with cardiac disease who are implanted with a cardiac rhythm management device (e.g., a conventional pacemaker, resynchronization pacemaker, defibrillator, combination device, or heart monitor) are apt to suffer changes in cardiopulmonary status over time, due to either disease progression or improvement. Such changes in cardiopulmonary status affect the optimal settings of pacing parameters as well as the appropriateness of other therapeutic options in treating the patient's disease. Traditionally, however, a patient's cardiopulmonary function is evaluated during a clinical examination which includes exercise testing as well as other techniques. This means that changes in a patient's cardiopulmonary function may only be detected after the patient has become very symptomatic and undergone formal clinical evaluation.

DETAILED DESCRIPTION

Figure 1:
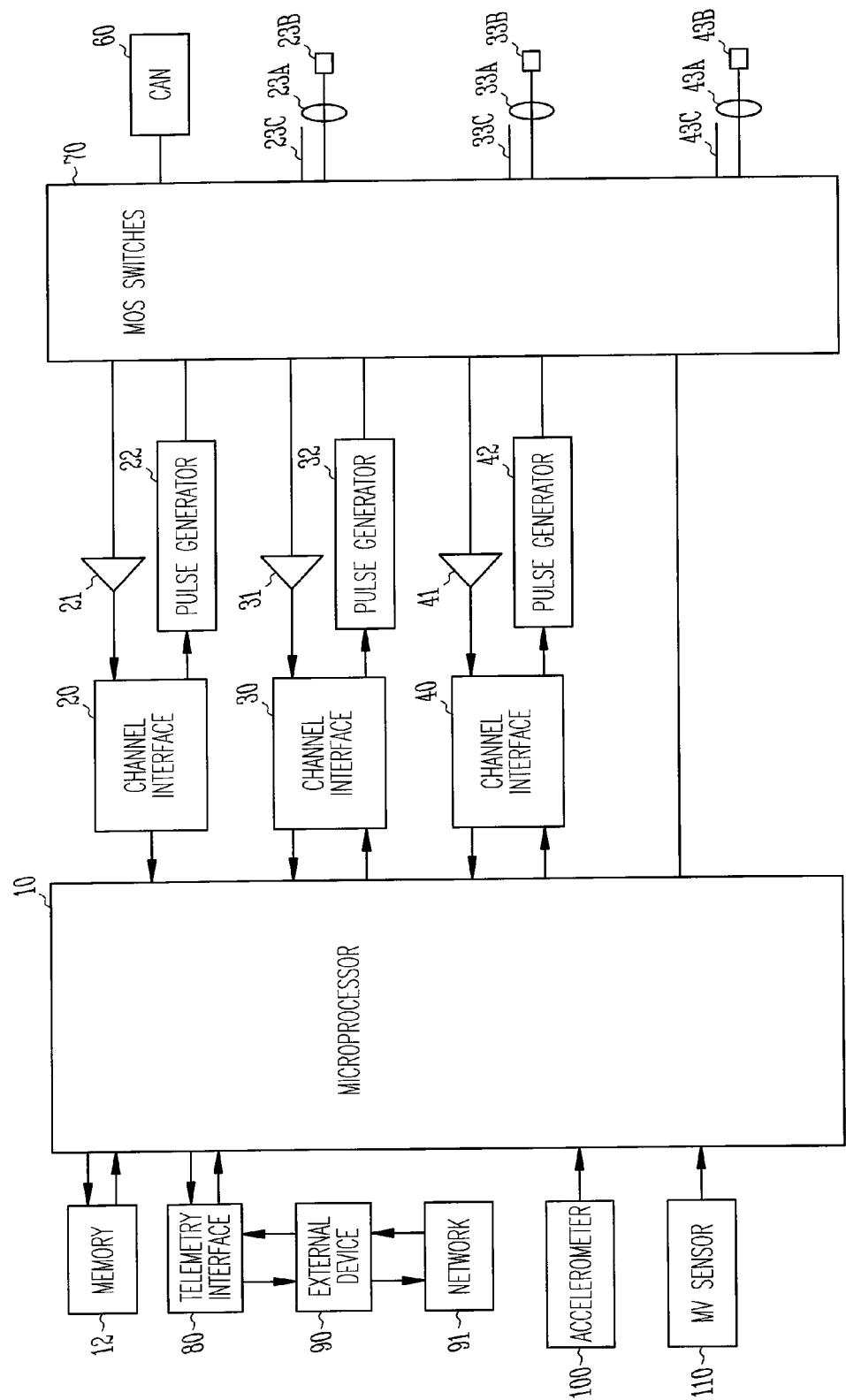
FIG. 1 is a block diagram of an exemplary cardiac rhythm management device.

The present disclosure relates to an implantable cardiac device which is configured to collect data for assessing a patient's cardiopulmonary function status using the device's sensing capabilities. Although cardiopulmonary function is by definition dependent upon both cardiac and lung function, what is of primary interest in a patient with cardiac disease is the adequacy of the patient's cardiac output in meeting metabolic demand. An indication of the adequacy of cardiac output may be obtained by comparing the workload performed by the body with a metabolic response parameter, where the latter is a physiological parameter which is regulated by the body in response to changing metabolic demand and is reflective of the extent to which metabolic needs are being met by the cardiopulmonary system. Assessment of cardiopulmonary function status may be performed by collecting measurements of activity level and a metabolic response parameter over time and then determining how the metabolic response parameter changes with respect to changes in activity level.

A measure of the absolute workload performed by a subject which is independent from the subject's individual physiology can be obtained from an activity level sensor such as an accelerometer or other type of motion sensor. Cardiac rhythm management devices are commonly equipped with an accelerometer to measure physical activity levels for use in rate-adaptive pacing modes. One example of a metabolic response parameter is intrinsic heart rate. If the body senses that cardiac output should be increased to meet metabolic demand, regulatory mechanisms cause the heart rate to increase. Heart rate, however, cannot be used as a metabolic response parameter for assessing cardiopulmonary function in pacemaker patients who are not chronotropically competent and whose heart rates are determined by the programmed escape intervals of the pacemaker. For these patients, a suitable metabolic response parameter is minute ventilation, where the term minute ventilation as used herein should be taken to include any measure of respiratory volume rate. Minute ventilation is regulated by respiratory control centers located in the brainstem which respond to, among other things, the pH of the blood. If the oxygen supplied to body tissues at a given activity level is inadequate to sustain the activity, the tissues resort to anaerobic metabolism which produces lactic acid as a by product. Increased production of lactic acid lowers the pH of the blood and causes the respiratory control centers to increase the respiratory volume rate. Thus, if a patient's cardiopulmonary function worsens, the minute ventilation at a given activity level will increase. An improvement in cardiopulmonary function, on the other hand, is reflected by a decreased minute ventilation a given activity level.

In one embodiment, the device constructs a historical record of activity level versus minute ventilation, referred to as a minute ventilation response profile. The minute ventilation response profile may be stored in the device's memory and later downloaded for use by a clinician in evaluating the cardiopulmonary function status of the patient and determining if any trend is present. The device may also be programmed to evaluate the patient's minute ventilation response by computing one or more minute ventilation response parameters, either on a continuous basis, at periodic intervals, when triggered by particular detected events, or when commanded to do so via telemetry. The device may then compare the computed minute ventilation response parameter to a normal range in order to assess the patient's cardiopulmonary status in real-time. If the device determines that the minute ventilation response is out of the normal range and that some type of intervention may be warranted, an alarm flag is set. (An alarm flag is any type of internal indication of the out of range condition which is stored in the device's memory.) The device may then transmit the relevant information via a telemetry link to clinical personnel, either when interrogated by an external programmer or immediately over a patient management network as described below.

As aforesaid, in order to evaluate a patient's minute ventilation response, one or more minute ventilation response parameters may be derived from the minute ventilation and activity level measurements. One example of a minute ventilation response parameter is the minute ventilation response slope, defined as the ratio of an incremental change in minute ventilation corresponding to an incremental change in activity level. Minute ventilation response slopes may be derived from the minute ventilation response profile for a plurality of different activity level ranges. Another minute ventilation response parameter could be a measure of the trend in minute ventilation response slope changes over some period time. In order to assess cardiopulmonary function, the minute ventilation response parameter(s) may be compared with normal ranges defined by upper and lower limit values. The range of the minute ventilation response parameter which is considered normal may be pre-specified, either in accordance with the average values in a representative population or as specifically derived for an individual patient, or may be computed from minute ventilation and accelerometer data collected by the device over some period of time. For example, an increase in a minute ventilation response slope above some limit may indicate that the patient is worsening and should be treated with additional device therapy and/or drug therapy in order to improve the slope. A decrease in the minute ventilation response slope, on the other hand, may indicate improved cardiac function.

In another embodiment, the device may be programmed to automatically adjust its operating parameters based upon the functional status assessment in order to provide more appropriate treatment to the patient. In the case of a device which delivers pacing therapy, the device may be programmed to automatically adjust pacing parameters such as the atrio-ventricular delay interval or other escape intervals, the biventricular delay interval, and rate-adaptive pacing parameters.

1. Exemplary Implantable Device Description

Assessment of cardiopulmonary function as described above may be implemented in any type of cardiac device (e.g., a conventional pacemaker, resynchronization pacemaker, defibrillator, combination device, or heart monitor) having the necessary sensing capabilities for measuring minute ventilation and activity level. Described below is an implantable cardiac rhythm management device which may be programmed to collect the needed data and perform a cardiopulmonary function assessment.

Cardiac rhythm management devices are contained within a housing which is usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site. A block diagram of an exemplary implantable cardiac rhythm management device is shown in FIG. 1. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. A telemetry interface 80 is also provided for enabling the controller to communicate with an external device 90 via a wireless telemetry link. The external device 90 may be an external programmer which can be used to program the implantable device as well as receive data from it or a remote monitoring unit. The external device 90 may also be interfaced to a patient management network 91 enabling the implantable device to transmit data and alarm messages to clinical personnel over the network. The network connection between the external device 90 and the patient management network 91 may be implemented by, for example, an internet connection, over a phone line, or via a cellular wireless link.

The embodiment shown in FIG. 1 has three sensing/pacing channels, where a pacing channel is made up of a pulse generator connected to an electrode while a sensing channel is made up of the sense amplifier connected to an electrode. A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. A sensing/pacing channel may include ring electrode 43a (33a or 23a) and tip electrode 43b (33b or 23b) of bipolar lead 43c (33c or 23c), sense amplifier 41 (31 or 21), pulse generator 42 (32 or 22), and a channel interface 40 (30 or 20). The channels may be configured as either atrial or ventricular channels. For example, the device may be configured for atrial pacing and either single ventricle or biventricular (resynchronization) pacing. The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A shock pulse generator (not shown) may also be interfaced to the controller for delivering defibrillation shocks between an electrode and the housing or can 60 as selected by the switch matrix. In the illustrated embodiment, the device is equipped with bipolar leads that include two electrodes which are used for outputting a pacing pulse and/or sensing intrinsic activity. Other embodiments may employ unipolar leads with single electrodes for sensing and pacing which are referenced to the device housing or can 60 (or another electrode) by the switch matrix 70.

The controller 10 controls the overall operation of the device in accordance with programmed instructions stored in memory and with information derived from the sensing channels. The voltages sensed by the sensing electrodes are electrogram signals that are analogous to a surface ECG and provide a temporal record of cardiac depolarization and repolarization that occurs during either intrinsic or paced beats. The sensing circuitry of the pacemaker generates chamber sense signals (i.e., atrial or ventricular senses) when voltages sensed by the electrodes of a particular channel exceed a specified threshold. The controller 10 interprets sense signals from the sensing channels in order to detect arrhythmias and to control the delivery of paces in accordance with a pacing algorithm that employs such senses to trigger or inhibit pacing. Most pacing modes are so-called demand modes where a heart chamber is paced upon expiration of an escape interval without receipt of a sense from that chamber. For example, in an atrial triggered mode, an atrial sense initiates an AV escape interval so that one or both ventricles are then paced upon expiration of the interval if no intrinsic ventricular activity occurs beforehand. The ventricles may also be paced upon expiration of an escape interval initiated by a ventricular sense or pace, and the atria may be paced by a ventriculoatrial escape interval initiated by a ventricular sense or pace.

Also interfaced to the controller are a minute ventilation sensor 110 and an accelerometer 100 for use in measuring a parameter related to the patient's exertion level and adjusting the pacing rate of the device accordingly in rate-adaptive pacing modes. The accelerometer and minute ventilation sensor produce a signal which approximates the patient's exertion level by measuring body activity and respiratory volume rate, respectively. The minute ventilation sensor measures the respiratory volume by injecting bursts of excitation current between excitation electrodes and measuring a transthoracic voltage drop to derive a signal proportional to the transthoracic impedance. (A particular minute ventilation sensor is described in U.S. Pat. No. 6,161,042, assigned to the assignee of the present application and hereby incorporated by reference in its entirety.) In a rate-adaptive pacing mode, one or more escape intervals are adjusted in accordance with a measured exertion level so that the pacing rate varies with metabolic demand. The modified pacing rate dictated by a rate-adaptive algorithm is referred to as the sensor-indicated rate. The rate-adaptive algorithm calculates the sensor-indicated rate by mapping a measured exertion level to a heart rate in accordance with a function referred to as the response factor.

2. Exemplary Implementation

Figure 2:
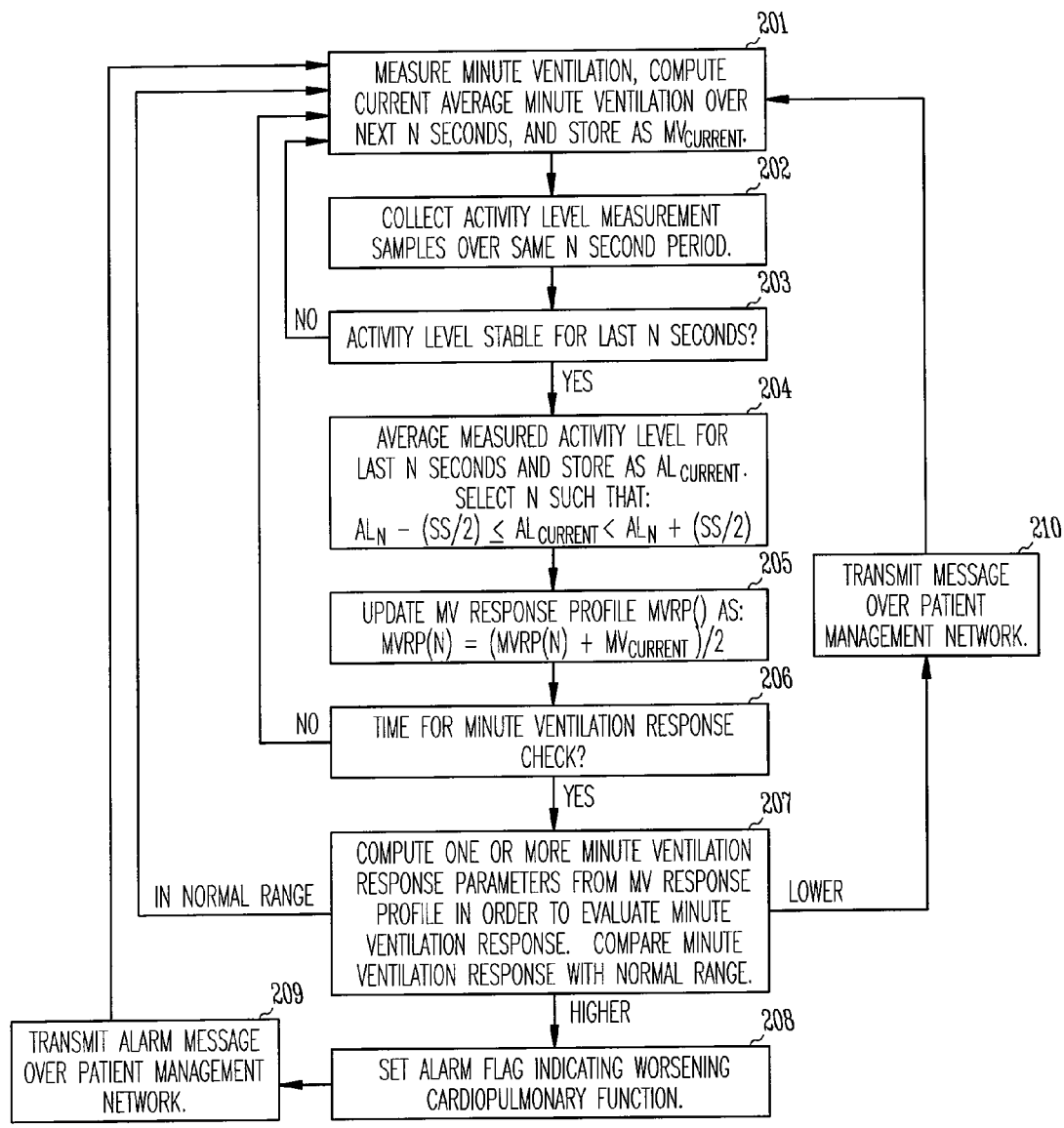
FIG. 2 illustrates an exemplary algorithm for monitoring cardiopulmonary functional status.

There are many ways in which an implantable device may implement and use the technique for assessing cardiopulmonary function as described above. Illustrated in FIG. 2 is one particular exemplary algorithm for assessing cardiopulmonary function which could be implemented in a cardiac rhythm management device by appropriate programming of the device controller. In an alternative embodiment, part of the processing burden in executing the algorithm may be assumed by an external programmer in communication with the device. The device is programmed to collect measured activity levels and corresponding minute ventilation in order to construct a minute ventilation response profile which reflects how the patient's minute ventilation varies with activity level. In this example, the minute ventilation response profile is a data structure MVRP( ) containing a plurality of minute ventilations indexed by an integer n, where n=0 to K. Each integer n corresponds to one of K discrete activity levels $AL_n$, where n=0 corresponds to no activity and n=K corresponds to the maximum activity level. Each activity level $AL_n$ is separated by a specified step size SS such that:

$$AL_{n+1}=AL_n+SS \text{ for } n=0 \text{ to } K-1$$

The minute ventilation response profile MVRP is constructed and updated by measuring a current minute ventilation, measuring a current activity level to determine an integer n such that the current activity level is close to $AL_n$, and then updating the entry for MVRP(n) with the current minute ventilation.

Starting at step 201, thoracic impedance measurements are made and used to compute an average minute ventilation over the next N seconds. The average minute ventilation thus computed is stored as $MV_{current}$. Simultaneously with the computation of the average minute ventilation, the device collects corresponding activity level measurements over the same N second period at step 202, where the activity level measurements are samples of the accelerometer output taken at some sampling interval. At step 203, the device determines whether or not the collected activity level measurements meet some predefined stability criterion. For example, a variance or similar statistic of the measurements could be computed and compared with a limit value. If the activity level is judged as not sufficiently stable, the device returns to step 201 to collect minute ventilation and activity level measurements for the next N second interval. If, instead, the activity level is judged to have been stable for the last N seconds, the average of the activity level measurement samples over the last N seconds is stored as $AL_{current}$ at step 204, and an integer n is selected such that:

$$AL_n(SS/2) \leq AL_{current} < AL_n+(SS/2)$$

At step 205, the minute ventilation response profile MVRP( ) is updated as:

$$MVRP(n)=(MVRP(n)+MV_{current})/2$$

At step 206, the device determines whether it is time to check the patient's minute ventilation response, as determined by either a command input or expiration of a specified time interval. If so, the device evaluates the patient's minute ventilation response at step 207 by computing one or more minute ventilation response parameters (such as a minute ventilation response slope) from the minute ventilation response profile and comparing the parameter(s) with normal ranges. If the minute ventilation response is within the normal range, the device returns to step 201. If the minute ventilation response is above the normal range, an alarm flag indicating a worsening cardiopulmonary function is set at step 208, an alarm message is transmitted over the patient management network at step 209, and the device returns to step 201. If the minute ventilation response is below the normal range an improving functional status is assumed and the device returns to step 201 after transmitting a message indicating the change in condition over the patient management network at step 210.

The device may also be programmed to automatically adjust pacing parameters in accordance with detected changes in minute ventilation response. The device may be programmed, for example, to decrease the lower rate limit interval (i.e., the minimum interval between ventricular beats permitted by the pacemaker) and/or decrease the AV delay interval by specified step sizes upon detection of a minute ventilation response which has worsened to a specified extent. The rate-adaptive response factor could also be adjusted in manner which increases the frequency of pacing. In the case of resynchronization pacing, the device could also be programmed to adjust the biventricular offset interval by a specified amount and in a specified direction (either an increase or a decrease) if the minute ventilation response worsens to a specified extent. The device could also initiate cardiac resynchronization therapy or other types of therapies deliverable by the device such as drug delivery when a cardiopulmonary function assessment indicates the therapy is warranted. The device may also be programmed to adjust pacing parameters in an opposite direction if a patient's cardiopulmonary function has improved to a specified extent. For example, it may be desirable to increase the lower rate limit interval, increase the AV delay interval, and/or decrease the rate-adaptive response factor in order to decrease the frequency of pacing upon detection of improved cardiopulmonary function.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. An implantable medical device, comprising:
   a controller;
   one or more sensing/pacing channels, wherein the controller is programmed to control the delivery of pacing pulses in accordance with an atrial-triggered mode such that a ventricular pace is delivered upon expiration of an escape interval designated as the AV delay interval;
   a minute ventilation sensor interfaced to the controller;
   an activity level sensor interfaced to the controller for measuring a parameter related to a patient's level of physical activity;
   wherein the controller is programmed to construct a historical record of activity level versus minute ventilation, referred to as a minute ventilation response profile;
   wherein the controller is further programmed to monitor a patient's cardiopulmonary functional status by computing a minute ventilation response slope from the minute ventilation response profile, defined as the ratio of an incremental change in minute ventilation to an incremental change in measured activity level, and compare the minute ventilation response slope to a specified limit value; and,
   wherein the controller is further programmed to decrease a lower rate limit interval upon detecting that the patient's minute ventilation response slope has worsened to a specified extent.

2. The device of claim 1 wherein the minute ventilation response profile is a data structure containing a plurality of minute ventilations, each minute ventilation being associated with a discrete activity level.

3. The device of claim 2 wherein the minute ventilation response profile is updated by averaging a currently measured minute ventilation over an N second interval and associating the averaged minute ventilation with an activity level corresponding to an average of a currently measured activity level over the N second interval.

4. The device of claim 3 wherein the minute ventilation response profile is updated only if activity level measurements taken over the N second interval meet a predefined stability criterion.

5. The device of claim 4 wherein the predefined stability criterion comprises computing a statistic of the measurements and comparing the statistic with a limit value.

6. The device of claim 1 wherein the controller is programmed to set an alarm flag if the minute ventilation response slope is not within a normal range as defined by upper and lower limit values.

7. The device of claim 6 further comprising:
   a telemetry interface for communicating with a remote monitoring device; and,
   wherein the controller is programmed to send an alert message via the telemetry interface if an alarm flag is set.

8. The device of claim 1 wherein the controller is further programmed to adjust the AV delay interval upon detecting that the patient's minute ventilation response slope has changed to a specified extent.

9. The device of claim 1 wherein the controller is further programmed to adjust a rate-response factor used in rate-adaptive pacing so as to increase the frequency of pacing upon detection of an increased minute ventilation response slope.

10. The device of claim 1 further comprising:
    sensing/pacing channels for delivering cardiac resynchronization pacing in the form of biventricular pacing with a specified biventricular offset interval; and,
    wherein the controller is further programmed to adjust the biventricular offset interval upon detection of a change in the minute ventilation response slope to a specified extent.

11. A method for operating an implantable medical device, comprising:
    delivering pacing pulses in accordance with an atrial-triggered mode such that a ventricular pace is delivered upon expiration of an escape interval designated as the AV delay interval;
    measuring a parameter related to a patient's level of physical activity;
    measuring a patient's minute ventilation;

constructing a historical record of activity level versus minute ventilation, referred to as a minute ventilation response profile;

monitoring a patient's cardiopulmonary functional status by computing a minute ventilation response slope from the minute ventilation response profile, defined as the ratio of an incremental change in minute ventilation to an incremental change in measured activity level, and comparing the minute ventilation response slope to a specified limit value; and, decreasing a lower rate limit interval upon detecting that the patient's minute ventilation response slope has worsened to a specified extent.

12. The method of claim 11 wherein the minute ventilation response profile is a data structure containing a plurality of minute ventilations, each minute ventilation being associated with a discrete activity level.

13. The method of claim 12 wherein the minute ventilation response profile is updated by averaging a currently measured minute ventilation over an N second interval and associating the averaged minute ventilation with an activity level corresponding to an average of a currently measured activity level over the N second interval.

14. The method of claim 13 wherein the minute ventilation response profile is updated only if activity level measurements taken over the N second interval meet a predefined stability criterion.

15. The device of claim 14 wherein the predefined stability criterion comprises computing a statistic of the measurements and comparing the statistic with a limit value.

16. The method of claim 11 further comprising setting an alarm flag if the minute ventilation response slope is not within a normal range as defined by upper and lower limit values.

17. The method of claim 16 further comprising send an alert message via a telemetry interface if an alarm flag is set.

18. The method of claim 11 further comprising adjusting the AV delay interval upon detecting that the patient's minute ventilation response slope has changed to a specified extent.

19. The method of claim 11 further comprising adjusting a rate-response factor used in rate-adaptive pacing so as to increase the frequency of pacing upon detection of an increased minute ventilation response slope.

20. The method of claim 11 further comprising:

delivering cardiac resynchronization pacing in the form of biventricular pacing with a specified biventricular offset interval; and, adjusting the biventricular offset interval upon detection of a change in the minute ventilation response slope to a specified extent.

* * * * *